United States Patent
Yamada

(10) Patent No.: US 10,322,078 B2
(45) Date of Patent: Jun. 18, 2019

(54) COSMETIC COMPOSITION CONTAINING 3-O-ALKYL-L-ASCORBIC ACID OR SALT THEREOF

(71) Applicant: AJINOMOTO CO., INC., Tokyo (JP)

(72) Inventor: Mandai Yamada, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 179 days.

(21) Appl. No.: 15/374,117

(22) Filed: Dec. 9, 2016

(65) Prior Publication Data

US 2017/0087078 A1 Mar. 30, 2017

Related U.S. Application Data

(63) Continuation of application No. PCT/JP2015/066687, filed on Jun. 10, 2015.

(30) Foreign Application Priority Data

Jun. 10, 2014 (JP) ................. 2014-119992

(51) Int. Cl.

| | |
|---|---|
| *A61K 8/67* | (2006.01) |
| *A61K 8/34* | (2006.01) |
| *A61K 8/37* | (2006.01) |
| *A61K 8/39* | (2006.01) |
| *A61K 8/44* | (2006.01) |
| *A61Q 19/02* | (2006.01) |
| *A61K 8/86* | (2006.01) |
| *A61K 8/31* | (2006.01) |
| *A61K 8/42* | (2006.01) |
| *A61K 8/92* | (2006.01) |

(52) U.S. Cl.
CPC ............... *A61K 8/676* (2013.01); *A61K 8/31* (2013.01); *A61K 8/34* (2013.01); *A61K 8/37* (2013.01); *A61K 8/39* (2013.01); *A61K 8/42* (2013.01); *A61K 8/44* (2013.01); *A61K 8/67* (2013.01); *A61K 8/86* (2013.01); *A61K 8/922* (2013.01); *A61Q 19/02* (2013.01)

(58) Field of Classification Search
CPC combination set(s) only.
See application file for complete search history.

(56) References Cited

U.S. PATENT DOCUMENTS

2011/0213030 A1* 9/2011 Shinto ................. A61K 8/0212
514/474

FOREIGN PATENT DOCUMENTS

| EP | 2 292 208 A1 | 3/2011 |
|---|---|---|
| JP | 58-57373 A | 4/1983 |
| JP | 61-207312 A | 9/1986 |
| JP | 62-226910 A | 10/1987 |
| JP | 3-133914 A | 6/1991 |
| JP | 11-199425 A | 7/1999 |
| JP | 11-199426 A | 7/1999 |
| JP | 2004-339133 A | 12/2004 |
| WO | WO 2009/145300 A1 | 12/2009 |
| WO | WO 2013/018491 A1 | 2/2013 |

OTHER PUBLICATIONS

International Search Report dated Aug. 25, 2015 in PCT/JP2015/066687.
Extended European Search Report dated Feb. 12, 2018 in Patent Application No. 15806749.6, citing document AO therein, 5 pages.

* cited by examiner

*Primary Examiner* — Ali Soroush
(74) *Attorney, Agent, or Firm* — Oblon, McClelland, Maier & Neustadt, L.L.P.

(57) ABSTRACT

The present invention provides a cosmetic composition containing (A) 3-O-alkyl-L-ascorbic acid wherein the alkyl group has 8-12 carbon atoms or a salt thereof, (B) one or more kinds of nonionic surfactants selected from the group consisting of polyoxyethylene polyoxypropylene alkyl ether, polyoxyethylene sorbitan fatty acid ester, polyoxyethylene alkyl ether and polyoxyethylene alkenyl ether, and having an HLB value of 12.5-17, and (C) one or more kinds of oil agents selected from the group consisting of amino acid ester, dimer acid ester, hydroxy acid ester, alkyl glyceryl ether and alkenyl glyceryl ether, which is superior in solubilization stability, preservation stability and sense of use, and free of time-dependent development of an odor which poses a problem when in use.

18 Claims, No Drawings

COSMETIC COMPOSITION CONTAINING 3-O-ALKYL-L-ASCORBIC ACID OR SALT THEREOF

CROSS REFERENCES TO RELATED APPLICATIONS

This application is a continuation of International Patent Application No. PCT/JP2015/066687, filed on Jun. 10, 2015, and claims priority to Japanese Patent Application No. 2014-119992, filed on Jun. 10, 2014, both of which are incorporated herein by reference in their entireties.

BACKGROUND OF THE INVENTION

Field of the Invention

The present invention relates to a cosmetic composition containing 3-O-alkyl-L-ascorbic acid or a salt thereof, which composition is superior in solubilization stability, preservation stability and the sense of use.

Discussion of the Background

Pigmentation of skin, which is observed in black spot, freckle, dark skin and the like, is considered to be generally caused by overproduction of melanin pigment by melanin pigment-producing cells in the skin. To improve or prevent pigmentation due to overproduction of melanin pigment, cosmetics containing L-ascorbic acid or a salt thereof have conventionally been proposed.

However, L-ascorbic acid and a salt thereof have problems in stability over time, odor and the like, since they develop color over time and produce odor and the like. As brightening agents that improve these problems, ascorbic acid derivatives such as 3-O-alkyl-L-ascorbic acid (patent document 1) and the like have been proposed.

However, since water solubility of alkylether derivatives of ascorbic acid such as 3-O-alkyl-L-ascorbic acid and the like decreases markedly, it is difficult to produce transparent cosmetics containing an ascorbic acid derivative and capable of maintaining the solubilized state. Also, preservation stability, sense of use and odor thereof are not satisfactory yet.

With such background, patent document 2 proposes cosmetics superior in preservation stability and brightening action, by blending 3-O-alkyl-L-ascorbic acid and a component with a skin activating effect. However, preservation stability was evaluated based only on the maintenance of brightening activity (tyrosinase activity inhibition rate) as an index, and solubilization stability, sense of use and odor are not specifically described at all.

Also, patent document 3 proposes cosmetics containing 3-O-alkyl-L-ascorbic acid and an anti-inflammatory agent, and recites skin lotion containing 3-O-ethyl-L-ascorbic acid, glycyrrhetinic acid, and polyoxyethylene(20)sorbitan monolaurate as an example. While patent document 3 describes that the aforementioned skin lotion was stable after preservation at 40° C. for 3 months, it does not refer to the sense of use.

DOCUMENT LIST

Patent Documents patent document 1: JP-A-S58-57373
patent document 2: JP-A-S61-207312
patent document 3: JP-A-H11-199426

SUMMARY OF THE INVENTION

Problems to be Solved by the Invention

Therefore, the present invention aims to provide a cosmetic composition containing 3-O-alkyl-L-ascorbic acid or a salt thereof and having a brightening action, which is superior in solubilization stability, preservation stability and sense of use, and is free of time-dependent development of an odor which poses a problem when in use.

Means of Solving the Problems

The present inventors have conducted intensive studies in an attempt to solve the above-mentioned problems and found that a cosmetic composition containing (A) particular 3-O-alkyl-L-ascorbic acid or a salt thereof, (B) one or more kinds of nonionic surfactants selected from the group consisting of polyoxyethylene polyoxypropylene alkyl ether, polyoxyethylene sorbitan fatty acid ester, polyoxyethylene alkyl ether and polyoxyethylene alkenyl ether, and having a particular HLB value, and (C) one or more kinds of oil agents selected from the group consisting of amino acid ester, dimer acid ester, hydroxy acid ester, alkyl glyceryl ether and alkenyl glyceryl ether is superior in solubilization stability, preservation stability and sense of use, and further, that the time-dependent development of an odor is favorably suppressed in the cosmetic composition and the composition poses no problem in use, which resulted in the completion of the present invention.

That is, the present invention relates to the following [1]-[13].

[1] A cosmetic composition comprising (A) 3-O-alkyl-L-ascorbic acid wherein the alkyl group has 8-12 carbon atoms or a salt thereof, (B) one or more kinds of nonionic surfactants selected from the group consisting of polyoxyethylene polyoxypropylene alkyl ether, polyoxyethylene sorbitan fatty acid ester, polyoxyethylene alkyl ether and polyoxyethylene alkenyl ether, and having an HLB value of 12.5-17, and (C) one or more kinds of oil agents selected from the group consisting of amino acid ester, dimer acid ester, hydroxy acid ester, alkyl glyceryl ether and alkenyl glyceryl ether.

[2] The cosmetic composition of the above-mentioned [1], wherein the polyoxyethylene polyoxypropylene alkyl ether is an alkylether of polyoxyethylene polyoxypropylene glycol having an average polymerization degree of ethylene oxide of 12-30 and an average polymerization degree of propylene oxide of 2-8, and the alkyl group is straight chain or branched chain alkyl having about 10-16 carbon atoms.

[3] The cosmetic composition of the above-mentioned [1], wherein the polyoxyethylene sorbitan fatty acid ester is a monoester of sorbitan added with 20 mol-40 mol of ethylene oxide on average per 1 mol of sorbitan, and a saturated or unsaturated fatty acid having 12-18 carbon atoms.

[4] The cosmetic composition of the above-mentioned [1], wherein the polyoxyethylene alkyl ether is an alkylether of polyethylene glycol having an average polymerization degree of ethylene oxide of 9-30, and the alkyl group is a straight chain or branched chain alkyl having 12-24 carbon atoms.

[5] The cosmetic composition of the above-mentioned [1], wherein the polyoxyethylene alkenyl ether is an alkenylether of polyethylene glycol having an average polymerization degree of ethylene oxide of 9-30, and the alkenyl group is a straight chain or branched chain alkenyl having 12-24 carbon atoms.

[6] The cosmetic composition of any of the above-mentioned [1]-[5], wherein the amino acid ester is an ester of N-acylamino acid and one or more kinds of alcohol selected from the group consisting of branched chain saturated lower alcohol having 3-5 carbon atoms, branched chain saturated aliphatic alcohol having 16-24 carbon atoms and sterol.

[7] The cosmetic composition of any of the above-mentioned [1]-[5], wherein the dimer acid ester is an ester of dimer dilinoleic acid and one or more kinds of alcohol selected from the group consisting of branched chain saturated lower alcohol having 3-5 carbon atoms, straight chain or branched chain saturated aliphatic alcohol having 16-22 carbon atoms and sterol.

[8] The cosmetic composition of any of the above-mentioned [1]-[5], wherein the hydroxy acid ester is an ester of aliphatic hydroxycarboxylic acid having 0.2-18 carbon atoms and branched chain saturated aliphatic alcohol having 8-18 carbon atoms.

[9] The cosmetic composition of any of the above-mentioned [1]-[5], wherein the alkyl glyceryl ether is a glyceryl ether having an alkyl group having 8-22 carbon atoms.

[10] The cosmetic composition of any of the above-mentioned [1]-[5], wherein the alkenyl glyceryl ether is a glyceryl ether having an alkenyl group having 8-22 carbon atoms.

[11] The cosmetic composition of any of the above-mentioned [1]-[10], which comprises 0.01 wt %-10 wt % of (A) 3-O-alkyl-L-ascorbic acid or a salt thereof relative to the total amount of the cosmetic composition.

[12] The cosmetic composition of any of the above-mentioned [1]-[11], which comprises 0.01 wt %-10 wt % of (B) nonionic surfactant relative to the total amount of the cosmetic composition.

[13] The cosmetic composition of any of the above-mentioned [1]-[12], which comprises 0.01 wt %-5 wt % of (C) oil agent relative to the total amount of the cosmetic composition.

Effect of the Invention

The cosmetic composition of the present invention is superior in the solubilization stability of 3-O-alkyl-L-ascorbic acid or a salt thereof, has high transparency, provides a sufficient brightening action, if free of stickiness and is superior in the sense of use.

In addition, the cosmetic composition of the present invention is superior in the preservation stability, and time-course development of color or odor, which poses problems in use, is not found with the cosmetic composition of the present invention.

DETAILED DESCRIPTION OF THE PREFERRED EMBODIMENTS

The cosmetic composition of the present invention contains 3-O-alkyl-L-ascorbic acid wherein the alkyl group has 8-12 carbon atoms or a salt thereof as component (A).

The above-mentioned 3-O-alkyl-L-ascorbic acid is a compound wherein the 3-position hydroxyl group of the L-ascorbic acid is etherified with an alkyl group having 8-12 carbon atoms. The alkyl group having 8-12 carbon atoms may be any of a straight chain alkyl group and a branched chain alkyl group. Examples thereof include n-octyl, isooctyl, 2-ethylhexyl, n-nonyl, isononyl, n-decyl, isodecyl, n-undecyl, isoundecyl, n-dodecyl, isododecyl and the like. Preferred are n-octyl, isooctyl, 2-ethylhexyl, n-dodecyl, isododecyl and the like, and more preferred are n-octyl, n-dodecyl and the like.

When the alkyl group of 3-O-alkyl-L-ascorbic acid is an alkyl group having not less than 13 carbon atoms, good solubilization stability is difficult to afford. When the above-mentioned alkyl group has not more than 7 carbon atoms, it is not preferable in view of the odor.

While the above-mentioned salt of 3-O-alkyl-L-ascorbic acid is not particularly limited as long as it is a pharmaceutically acceptable salt, examples thereof include alkali metal salts such as lithium salt, sodium salt, potassium salt and the like, alkaline earth metal salts such as magnesium salt, calcium salt and the like, amino acid salts such as ammonium salt, arginine salt, histidine salt, lysin salt and the like, and the like. Sodium salt, potassium salt, magnesium salt, calcium salt and the like are preferable, and sodium salt, potassium salt and the like are more preferable.

The 3-O-alkyl-L-ascorbic acid wherein the alkyl group has 8-12 carbon atoms and a salt thereof are compounds known per se, and can be produced according to a method known per se such as the method described in JP-A-S58-57373 and the like. In the present invention, an appropriately-produced compound may be used, and a commercially available product can also be used.

For the cosmetic composition of the present invention, one kind may be selected from the above-mentioned 3-O-alkyl-L-ascorbic acid and a salt thereof and used singly as component (A), or two or more kinds may be selected and used in combination.

Component (A), i.e., 3-O-alkyl-L-ascorbic acid wherein the alkyl group has 8-12 carbon atoms or a salt thereof is preferably contained at 0.01 wt %-10 wt %, more preferably 0.1 wt %-3 wt %, relative to the total amount of the cosmetic composition of the present invention from the aspects of brightening action, solubilization stability and the like.

The cosmetic composition of the present invention contains, as component (B), one or more kinds of nonionic surfactants selected from the group consisting of polyoxyethylene polyoxypropylene alkyl ether, polyoxyethylene sorbitan fatty acid ester, polyoxyethylene alkyl ether and polyoxyethylene alkenyl ether, and having an HLB (Hydrophile-Lypophile balance) value of 12.5-17.

For the object of the present invention, the nonionic surfactant for component (B) preferably has an HLB value of 14-16.

Using the above-mentioned nonionic surfactant, a cosmetic composition having transparency and solubilization stability can be obtained.

In the present invention, as polyoxyethylene polyoxypropylene alkyl ether, one having an average polymerization degree of ethylene oxide of 12-30, and an average polymerization degree of propylene oxide of 2-8, wherein the alkyl group is straight chain Or branched chain alkyl having about 10-16 carbon atoms, is preferably used. Specifically, polyoxyethylene(15)polyoxypropylene(2)decyl ether, polyoxyethylene(20)polyoxypropylene(2)decyl ether, polyoxyethylene(30)polyoxypropylene(2)decyl ether, polyoxyethylene(20)polyoxypropylene(4)cetyl ether, polyoxyethylene(20)polyoxypropylene(8)cetyl ether and the like can be mentioned.

In the present invention, the above-mentioned polyoxyethylene polyoxypropylene alkyl ether to be used may be produced according to a production method known per se. It is convenient to use commercially available products such as "NIKKOL PBC-34" (HLB value=16.5), "NIKKOL PBC-44" (HLB value=12.5) (the above manufactured by Nikko Chemicals Co., Ltd.), "UNISAFE 20P-4" (HLB value=16.5), "UNISAFE 20P-8" (HLB value=12.5) (the above manufactured by NOF CORPORATION) and the like.

As the polyoxyethylene sorbitan fatty acid ester, a monoester of saturated or unsaturated fatty acid having about 12-18 carbon atoms and having an average addition mole number of ethylene oxide of about 20-40 per 1 mol of sorbitan is preferably used. Specific examples thereof include polyoxyethylene(20)sorbitan monolaurate, polyoxyethylene(20)sorbitan monomyristate, polyoxyethylene(20) sorbitan monopalmitate, polyoxyethylene(20)sorbitan monostearate, polyoxyethylene(20)sorbitan monoisostearate, polyoxyethylene(20)sorbitan mono coconut oil fatty acid ester, polyoxyethylene(20)sorbitan monooleate, polyoxyethylene(40)sorbitan monooleate and the like.

In the present invention, as the above-mentioned polyoxyethylene sorbitan fatty acid ester, one produced according to a production method known per se can also be used. It is convenient to use commercially available products such as "NIKKOL TL-10" (HLB value=16.9), "NIKKOL TP-10V" (HLB value=15.6), "NIKKOL TP-10EX" (HLB value=15.6), "NIKKOL TS-10V" (HLB value=14.9), "NIKKOL TI-10V" (HLB value=15.0), "NIKKOL TO-10V" (HLB value=15.0) (the above manufactured by Nikko Chemicals Co., Ltd.), "nonionic LT-221" (HLB value=16.7), "nonionic OT-221" (HLB value=15.7) (the above manufactured by NOF CORPORATION), "Rheodol TW-L120" (HLB value=16.7), "Rheodol TW-P120" (HLB value=15.6), "Rheodol TW-S120V" (HLB value=14.9), "Rheodol TW-0120V" (HLB value=15.0) (the above manufactured by Kao Corporation), "Sorgen TW-60F" (HLB value=14.9), "Sorgen TW-80V" (HLB value=15.0) (the above manufactured by DKS Co. Ltd.) and the like.

As polyoxyethylene alkyl ether or polyoxyethylene alkenyl ether, one having an average polymerization degree of ethylene oxide of 9-30, wherein the alkyl group or alkenyl group is straight chain or branched chain alkyl or alkenyl having about 12-24 carbon atoms, is preferably used. Specific examples thereof include polyoxyethylene(9)lauryl ether, polyoxyethylene(10)cetyl ether, polyoxyethylene(15) cetyl ether, polyoxyethylene(20)cetyl ether, polyoxyethylene(20)behenyl ether, polyoxyethylene(9)$C_{12-14}$ secondary alkylether, polyoxyethylene (12) $C_{12-14}$ secondary alkylether, polyoxyethylene(15)oleyl ether, polyoxyethylene(20) oleyl ether, polyoxyethylene(23)oleyl ether, polyoxyethylene(25)octyldodecyl ether, polyoxyethylene(25) decyltetradecyl ether, polyoxyethylene(30)cetyl ether, polyoxyethylene(30)stearyl ether, polyoxyethylene(30)behenyl ether and the like.

In the present invention, as the above-mentioned polyoxyethylene alkyl ether and polyoxyethylene alkenyl ether, those produced according to a production method known per se can also be used. It is convenient to use commercially available products such as "NIKKOL BL-9EX" (HLB value=14.5), "NIKKOL BC-10" (HLB value=13.5), "NIKKOL BC-15" (HLB value=15.5), "NIKKOL BC-20" (HLB value=17.0), "NIKKOL BT-9" (HLB value=13.5), "NIKKOL BT-12" (HLB value=14.5), "NIKKOL BB-20" (HLB value=16.5), "NIKKOL BO-15V" (HLB value=16.0), "NIKKOL BO-20V" (HLB value=17.0) (the above manufactured by Nikko Chemicals Co., Ltd.), "Emulmin LS-80". (HLB value=13.1), "Emulmin LS-90" (HLB value=13.6), "Emulmin NL-80" (HLB value=13.1), "Emulmin NL-90" (HLB value=13.6), "Emulmin NL-100" (HLB value=14.0), "Emulmin NL-110" (HLB value=14.4), "Emulmin 110" (HLB value=13.2), "Emulmin 140" (HLB value=14.2), "Emulmin 180" (HLB value=15.1), "Emulmin 200" (HLB value=15.5), "Emulmin 240" (HLB value=16.1) (the above manufactured by Sanyo Chemical Industries, Ltd.) and the like.

In the present invention, one kind may be selected from the above-mentioned nonionic surfactant and used singly, or two or more kinds may be selected and used in combination.

Component (B), i.e., one or more kinds of nonionic surfactants selected from the group consisting of polyoxyethylene polyoxypropylene alkyl ether, polyoxyethylene sorbitan fatty acid ester, polyoxyethylene alkyl ether and polyoxyethylene alkenyl ether, and having an HLB value of 12.5-17, is contained at preferably 0.01 wt %-10 wt %, more preferably 0.1 wt %-3 wt %, relative to the total amount of the cosmetic composition of the present invention, from the aspects of transparency and solubilization stability of the cosmetic composition.

The cosmetic composition of the present invention contains, as component (C), one or more kinds of oil agents selected from the group consisting of amino acid ester, dimer acid ester, hydroxy acid ester, alkyl glyceryl ether and alkenyl glyceryl ether.

An amino acid ester usable in the present invention is not particularly limited and any can be used as long as it is an ester formed from amino acid and alcohol. An ester formed with monovalent alcohol or sterol is preferable.

Examples of the amino acid that forms an amino acid ester include protein-constituting amino acids such as aliphatic amino acids (e.g., glycine, alanine, valine, leucine, isoleucine and the like); amino acids having a hydroxy group (e.g., serine, threonine and the like); sulfur-containing amino acids (e.g., methionine, cysteine and the like); amino acids having an amido group (e.g., asparagine, glutamine and the like); amino acids having an imino group (e.g., proline and the like); amino acids having an aromatic group (e.g., phenylalanine, tyrosine, tryptophan and the like); acidic amino acids (e.g., aspartic acid, glutamic acid and the like); basic amino acids (e.g., arginine, histidine, lysine and the like), and the like, as well as amino acids such as β-alanine, sarcosine (N-methylglycine), ornithine, creatine, γ-aminobutyric acid and the like.

The above-mentioned amino acid may be any of D form, L form, and DL form, and L form is preferable. Alanine, sarcosine and acidic amino acids (e.g., glutamic acid) are particularly preferable.

Furthermore, in the above-mentioned amino acid, the amino group may be substituted by an alkyl group or an acyl group. As such alkyl group, a lower alkyl group having about 1-3 carbon atoms such as methyl, ethyl and the like is preferable and, as the acyl group, an acyl group having about 8-18 carbon atoms such as octanoyl, decanoyl, lauroyl, myristoyl, palmitoyl, stearoyl, isostearoyl and the like is preferable.

In the present invention, an ester formed from N-acylamino acid wherein the amino group is substituted by the above-mentioned acyl group, and monovalent alcohol or sterol is more preferably used.

Examples of the monovalent alcohol that forms an ester with amino acid include saturated or unsaturated lower alcohol having up to about 5 carbon atoms such as ethanol, propanol, butanol, pentanol, isopropanol, isobutanol, 2-butanol, tert-butanol, isopentanol, isobutenol and the like, straight chain saturated aliphatic alcohol having about 8-24 carbon atoms such as octanol, decanol, undecanol, lauryl alcohol, myristyl alcohol, palmityl alcohol (cetanol), stearyl alcohol, behenyl alcohol, tetracosanol and the like, branched chain saturated aliphatic alcohol having about 8-24 carbon atoms such as 2-ethylhexanol, 2-decanol, 2-hexyldecanol, isostearyl alcohol, 2-octyldodecanol, 2-decyltetradecanol and the like, and unsaturated aliphatic alcohol having about 8-24 carbon atoms such as palmitoleyl alcohol, oleyl alcohol, linoleyl alcohol, linolenyl alcohol, docosenol and the like.

Examples of the sterol that forms an ester with amino acid include phytosterol such as sitosterol, campesterol, stigmasterol, brassicastero and the like; hydrogenated phytosterol obtained by hydrogenation of the aforementioned phytosterol; sterol derived from animal such as cholesterol, dihydrocholesterol, desmosterol, lathosterol, lanosterol, dihydrolanosterol, agnosterol and the like; sterol derived from fungus such as ergosterol and the like, and the like.

Of these, branched chain saturated lower alcohol having about 3-5 carbon atoms such as isopropanol and the like, branched chain saturated aliphatic alcohol having about 16-24 carbon atoms such as 2-hexyldecanol, isostearyl alcohol, 2-octyldodecanol, 2-decyltetradecanol and the like, and sterol such as phytosterol, cholesterol and the like are preferable.

Amino acid ester may be an ester formed by a mixture of amino acid, and two or more kinds selected from the group consisting of the above-mentioned monovalent alcohol and sterol.

When the amino acid is an acidic amino acid such as glutamic acid and the like, the ester of amino acid and monovalent alcohol or sterol may be a monoester or diester, and diester is more preferable.

In the present invention, an ester of N-acylamino acid, and one or more kinds of alcohol selected from the group consisting of branched chain saturated lower alcohol having 3-5 carbon atoms, branched chain saturated aliphatic alcohol having 16-24 carbon atoms and sterol is particularly preferably used. Examples of the amino acid ester include isopropyl N-lauroyl sarcosinate, N-myristoyl-N-methylalaninehexyldecyl, N-myristoyl-N-methyl-β-alanine(phytosterol/decyltetradecyl), i.e., ester of N-myristoyl-N-methyl-β-alanine and a mixture of phytosterol and decyltetradecanol, N-lauroylglutamic acid dihexyldecyl, N-lauroylglutamic acid diisostearyl, N-lauroylglutamic acid dioctyldodecyl, N-lauroylglutamic acid bis(hexyldecyl/octyldodecyl), i.e., diester of N-lauroylglutamic acid and a mixture of hexyldecanol and octyldodecanol, N-stearoylglutamic acid dioctyldodecyl, N-lauroylglutamic acid di(cholesteryl/octyldodecyl), i.e., diester of N-lauroylglutamic acid and a mixture of cholesterol and octyldodecanol, N-lauroylglutamic acid di(cholesteryl/behenyl/octyldodecyl), i.e., diester of N-lauroylglutamic acid and a mixture of cholesterol, behenyl alcohol and octyldodecanol, N-lauroylglutamic acid di(phytosteryl/octyldodecyl), i.e., diester of N-lauroylglutamic acid and a mixture of phytosterol and octyldodecanol, N-lauroylglutamic acid di(octyldodecyl/phytosteryl/behenyl), i.e., diester of N-lauroylglutamic acid and a mixture of octyldodecanol, phytosterol and behenyl alcohol and the like.

While these may be produced according to a production method known per se, commercially available products ("AMITER" series, "Eldew" series etc.) provided by Nihon Emulsion Co., Ltd., Ajinomoto Co., Inc. and so on the can be preferably used.

The dimer acid ester usable in the present invention is an ester which is formed by dimer acid and alcohol. Dimer acid is a known dibasic acid obtained by an intermolecular polymerization reaction of unsaturated fatty acid, which is industrially generally obtained by dimerizing unsaturated fatty acid having 11-22 carbon atoms or lower alcohol ester thereof with a clay catalyst and the like. A dimer acid obtained industrially contains a dibasic acid having about 36 carbon atoms as a main component. In the present invention, an ester of dimer dilinoleic acid is preferably used.

Examples of the alcohol that forms an ester with dimer acid include monovalent alcohol similar to alcohol that forms the above-mentioned amino acid ester and sterol, and branched chain saturated lower alcohol having about 3-5 carbon atoms such as isopropanol and the like, straight chain or branched chain saturated aliphatic alcohol having about 16-22 carbon atoms such as cetanol, stearyl alcohol, behenyl alcohol, isostearyl alcohol, 2-octyldodecanol and the like, and sterol such as phytosterol, cholesterol and the like are preferably used.

The ester of dimer acid may be an ester which is formed from a mixture of dimer acid, and two or more kinds selected from the group consisting of the above-mentioned monovalent alcohol and sterol. The ester of dimer acid is preferably a diester of dimer acid and the above-mentioned alcohol.

In the present invention, an ester of dimer dilinoleic acid, and one or more kinds of alcohol selected from the group consisting of branched chain saturated lower alcohol having 3-5 carbon atoms, straight chain or branched chain saturated aliphatic alcohol having 16-22 carbon atoms and sterol is more preferably used, and a diester of dimer dilinoleic acid, and one or more kinds of alcohol selected from the group consisting of branched chain saturated lower alcohol having 3-5 carbon atoms, straight chain or branched chain saturated aliphatic alcohol having 16-22 carbon atoms and sterol is particularly preferably used. Examples of the diester of dimer dilinoleic acid include dimer diisopropyl dilinoleate, dimer dilinoleic acid di(isostearyl/phytosteryl), i.e., diester of dimer dilinoleic acid, and a mixture of isostearyl alcohol and phytosterol, dimer dilinoleic acid di(phytosteryl/isostearyl/cetyl/stearyl/behenyl), i.e., diester of dimer dilinoleic acid, and a mixture of phytosterol, isostearyl alcohol, cetanol, stearyl alcohol and behenyl alcohol and the like.

These may be produced according to a production method known per se, and commercially available products provided by Kokyu Alcohol Kogyo Co., Ltd., NIPPON FINE CHEMICAL CO., LTD. and so on ("KAK DADIP-R", "Plandol" series etc.) can be preferably used.

The hydroxy acid ester usable in the present invention is an ester formed by hydroxy acid and alcohol.

While the hydroxy acid that forms hydroxy acid ester is not particularly limited as long as it is carboxylic acid having a hydroxyl group, and aliphatic hydroxycarboxylic acid having about 2-18 carbon atoms such as glycolic acid, lactic acid, tartronic acid, glyceric acid, 2-hydroxybutyric acid, 3-hydroxybutyric acid, 4-hydroxybutyric acid, malic acid, tartaric acid, citramalic acid, citric acid, isocitric acid, leucine acid, mevalonic acid, pantoic acid, ricinoleic acid and the like is preferable, and aliphatic hydroxydicarboxylic acid having about 3-6 carbon atoms such as tartronic acid, malic acid, tartaric acid, citramalic acid and the like is more preferable.

Examples of the alcohol that forms an ester with hydroxy acid include monovalent alcohol similar to the alcohol that forms the above-mentioned amino acid ester and sterol, and branched chain saturated aliphatic alcohol having about 8-18 carbon atoms, such as 2-ethylhexanol, isostearyl alcohol and the like, is preferably used.

When aliphatic hydroxydicarboxylic acid is used as hydroxy acid, a diester with the above-mentioned alcohol is preferable.

In the present invention, an ester of aliphatic hydroxycarboxylic acid having 2-18 carbon atoms and branched chain saturated aliphatic alcohol having 8-18 carbon atoms is more preferably used, a diester of aliphatic hydroxydicarboxylic acid having 3-6 carbon atoms and branched chain saturated aliphatic alcohol having 8-18 carbon atoms is further preferably used, and a diester of malic acid or tartaric acid and branched chain saturated aliphatic alcohol having 8-18 carbon atoms is particularly preferably used. Examples of the diester of malic acid or tartaric acid include diethylhexyl malate, diisostearyl malate and the like.

These may be produced according to a production method known per se, and commercially available products provided by Kokyu Alcohol Kogyo Co., Ltd., Nisshin 011110 Group, Ltd., ISP (Japan) Ltd. and so on ("Haimalate DIS", "Cosmol 222", "Ceraphyl 45" etc.) can be preferably used.

As alkyl glyceryl ether usable in the present invention, glyceryl ether having an alkyl group having about 8-22 carbon atoms is preferable, a monoether of glycerol and straight chain or branched chain saturated aliphatic alcohol having about 8-22 carbon atoms is more preferably used, and examples of the monoether include monooctyl glyceryl ether, mono 2-ethylhexyl glyceryl ether, monononyl glyceryl ether, monodecyl glyceryl ether, monoisodecyl glyceryl ether, monoundecyl glyceryl ether, monolauryl glyceryl ether, monomyristyl glyceryl ether, monocetyl glyceryl ether, monostearyl glyceryl ether, monoisostearyl glyceryl ether, monoarachidyl glyceryl ether, monobehenyl glyceryl ether and the like. Of these, monocetyl glyceryl ether, monostearyl glyceryl ether and monoisostearyl glyceryl ether are particularly preferably used.

As alkenyl glyceryl ether usable in the present invention, a glyceryl ether having an alkenyl group having about 8-22 carbon atoms is preferable, a monoether of glycerol, and straight chain or branched chain unsaturated aliphatic alcohol having about 8-22 carbon atoms is more preferably used, and examples of the monoether include monooctenyl glyceryl ether, monopalmitoleyl glyceryl ether, monooleyl glyceryl ether, monolinoleyl glyceryl ether, monolinolenyl glyceryl ether, monoricinoleyl glyceryl ether, monoerucyl glyceryl ether and the like. Of these, monooleyl glyceryl ether is particularly preferably used.

These may be produced according to a production method known per se, and commercially available products provided by Nikko Chemicals Co., Ltd., Kao Corporation and so on ("NIKKOL chimyl alcohol 100", "NIKKOL batyl alcohol 100", "NIKKOL batyl alcohol EX", "NIKKOL serachyl alcohol", "penetol GE-IS" etc.) can be preferably used.

In the present invention, as the oil agent for component (C), one kind may be selected from the group consisting of the above-mentioned amino acid ester, dimer acid ester, hydroxy acid ester, alkyl glyceryl ether and alkenyl glyceryl ether, and used singly, or two or more kinds may be selected and used in combination.

Component (C), i.e., one or more kinds of oil agents selected from the group consisting of amino acid ester, dimer acid ester, hydroxy acid ester, alkyl glyceryl ether and alkenyl glyceryl ether is/are preferably contained at 0.01 wt %-5 wt %, more preferably 0.03 wt %-1 wt %, relative to the total amount of the cosmetic composition of the present invention, particularly from the aspects of solubilization stability, preservation stability and sense of use.

For the object of the present invention, the above-mentioned components (A)-(C) are preferably contained such that the content ratios of component (B) and component (C) to component (A), that is, [content of component (B)/content of component (A)] and [content of component (C)/content of component (A)] in weight ratio are 1/5-5 and 1/20-1/2, more preferably 1/3-3 and 1/10-1/3, respectively.

The cosmetic composition of the present invention can contain, besides the above-mentioned components (A)-(C), additives generally blended in a cosmetic composition such as moisturizer, thickening/gelling agent, antiwrinkle/antiaging agent, cellular stimulant, anti-inflammatory agent, antioxidant, UV absorption/scattering agent, preservative, pH adjuster, colorant, flavor and the like, as long as the characteristics of the present invention are not impaired.

Examples of the moisturizer include polyvalent alcohol such as glycerol, 1,3-propanediol, sorbitol and the like; mucopolysaccharides such as sodium hyaluronate, chondroitin sulfate and the like; amino acids such as alanine, sodium pyrrolidonecarboxylate and the like or a salt thereof; and the like.

Examples of the thickening/gelling agent include polysaccharides such as carageenan, xanthan gum, gellan gum, locust bean gum and the like; cellulose derivatives such as hydroxyethylcellulose, methylcellulose, hydroxypropylmethylcellulose and the like; synthetic water-soluble polymers such as carboxyvinyl polymer, polyacrylic acid, polyvinylpyrrolidone and the like; and the like.

Examples of the antiwrinkle/antiaging agent include hydrolyzed eggshell membrane, atelocollagen, rice bran extract, rooibos extract and the like.

Examples of the cellular stimulant include deoxyribonucleic acid sodium salt, yeast extract, asian *ginseng* extract and the like.

Examples of the anti-inflammatory agent include allantoin, aloe vera extract, krantz aloe extract, camomile extract, licorice extract, dipotassium glycyrrhizate and the like.

Examples of the antioxidant include vitamin E such as tocopherol acetate, d-δ-tocopherol, dl-α-tocopherol, natural vitamin E and the like; polyphenols such as glucosylrutin, tannic acid and the like; gallic acids such as gallic acid, propyl gallate and the like and a derivative thereof; plant extracts such as Japanese basil leaf extract, sage leaf extract and the like; and the like.

Examples of the UV absorption/scattering agent include paradimethylaminobenzoate 2-ethylhexyl, oxybenzone-3(2-hydroxy-4-methoxybenzophenone), paramethoxycinnamic acid 2-ethylhexyl, 4-tert-butyl-4'-methoxydibenzoylmethane, titanium oxide and the like.

Examples of the preservative include sodium benzoate; phenoxyethanol; paraoxybenzoates such as methyl p-hydroxybenzoate, ethyl parahydroxybenzoate, propyl p-hydroxybenzoate and the like; and the like.

Examples of the pH adjuster include succinic acid, citric acid, sodium citrate, tartaric acid, sodium tartarate, sodium hydroxide, potassium hydroxide, triethanolamine, gluconolactone and the like.

Examples of the colorant include inorganic pigments such as iron blue, ultramarine blue, red iron oxide, black iron oxide, yellow iron oxide, talc, kaolin, manganese violet, carbon black and the like; natural dyes such as β-carotene, lycopene, shisonin, safflor yellow, shikonin, chlorophyll and the like, tar pigments such as red No. 102, red No. 201, Blue No. 202 and the like, lake pigments such as red No. 3 aluminum lake, yellow No. 4 aluminum lake, blue No. 1 barium lake and the like; and the like.

Examples of the flavor include natural flavors such as cinnamon oil, lavender oil, jasmine oil, peppermint oil, orange oil, rose oil and the like; synthetic flavors such as citronellol, eugenol, geraniol, menthol and the like; and the like.

One or more kinds of the above-mentioned additives selected according to the object can be contained in amounts generally used for cosmetic compositions, as long as the characteristics of the present invention are not impaired.

The cosmetic composition of the present invention containing 3-O-alkyl-L-ascorbic acid or a salt thereof shows good solubilization stability and good preservation stability, has high transparency, is free of stickiness and superior in the sense of use. Therefore, it can be provided preferably in a liquid or gel form, as skin lotion, serum or gel for brightening.

The cosmetic composition of the present invention can be produced according to a general production method of skin lotion, serum or gel in a liquid or gel form.

For example, in the case of skin lotion, it is prepared by successively adding the above-mentioned components (A)-(C) and other additives where necessary to purified water, stirring and mixing them to achieve uniform dissolution, and filtering the mixture. When the additive is an oil-soluble component, it is preferably added to and dissolved in component (C) in is advance and then added to purified water, or added to purified water after mixing with component (B). A powder such as inorganic pigment and the like is preferably mixed with purified water, and moisture dispersed by stirring.

In the case of a viscous serum, it can be produced by successively adding components (A)-(C) to purified water, uniformly dissolving them by mixing, and adding a thickening/gelling agent to increase viscosity, or adding and dissolving a thickening/gelling agent in a part of purified water, and then mixing the rest of purified water with a solution of components (A)-(C).

In the case of a gel, it can be prepared by adding components (A)-(C), and additives including a thickening/gelling agent to purified water, stirring and mixing same, and heating or cooling same as necessary to form a gel.

Other features of the invention will become apparent in the course of the following descriptions of exemplary embodiments which are given for illustration of the invention and are not intended to be limiting thereof.

EXAMPLES

The present invention is explained in more detail in the following by referring to Examples.

Experimental Example 1

Study of Influence of Alkyl Group of 3-O-Alkyl-L-Ascorbic Acid or Salt Thereof

An influence of a difference in the carbon number of alkyl group in 3-O-alkyl-L-ascorbic acid or a salt thereof on the transparency, solubilization stability, preservation stability and sense of use of a cosmetic composition was studied.

3-O-octyl (carbon number=8)-L-ascorbic acid, 3-O-dodecyl (carbon number=12)-L-ascorbic acid, and 3-O-hexadecyl (carbon number=16)-L-ascorbic acid in the amounts shown in Table 1 were added to water in the presence or absence of (B) polyoxyethylene(20)sorbitan monooleate (HLB value=15.0), and mixed to give each sample.

As polyoxyethylene(20)sorbitan monooleate, "NIKKOL TO-10V" (manufactured by Nikko Chemicals Co., Ltd.) was used.

Each sample was evaluated for transparency, solubilization stability, preservation stability, sense of use and odor as follows.

(1) Transparency

The appearance of each sample was observed immediately after preparation, and the transparency was evaluated according to the following criteria.

<Evaluation Criteria>
○; transparent
Δ; somewhat clouded
x; remarkably clouded (2) Solubilization Stability Each sample was preserved at 40° C. for 7 days, and the solubilization state was evaluated according to the following criteria.

<Evaluation Criteria>
○; 3-O-alkyl-L-ascorbic acid is solubilized well
Δ; 3-O-alkyl-L-ascorbic acid is slightly precipitated
x; 3-O-alkyl-L-ascorbic acid is remarkably precipitated (3) Preservation Stability Each sample was preserved at 40° C. for 7 days, the presence or absence and the level of coloration were observed, and evaluated according to the following criteria.

<Evaluation Criteria>
○; coloration is not observed
Δ; coloration is slightly observed
x; coloration is remarkably observed (4) Sense of Use Five panelists used each sample, made sensory evaluation of the sense of use (absence of stickiness) and graded according to the following evaluation criteria. The evaluation results are shown by "○" when the total evaluation point of 5 panelists is not less than 8 points, "Δ" when the total point is not less than 4 points and not more than 7 points, and "x" when the total point is not more than 3 points.

<Evaluation Criteria>
2 points; no stickiness
1 point; slight stickiness
0 point; clear stickiness (5) Odor Each sample was preserved at 40° C. for 7 days, and 5 panelists used each sample, made sensory evaluation of the odor felt on application and graded according to the following evaluation criteria. The evaluation results are shown by "○" when the total evaluation point of 5 panelists is not less than 8 points, "Δ" when the total point is not less than 4 points and not more than 7 points, and "x" when the total point is not more than 3 points.

<Evaluation Criteria>
2 points; no odor felt on application
1 point; slight odor felt on application
0 point; clear odor felt on application The results of this test are also shown in Table 1.

TABLE 1

| | | sample | | | | | |
|---|---|---|---|---|---|---|---|
| | component | 1 | 2 | 3 | 4 | 5 | 6 |
| (A) | 3-O-octyl-L-ascorbic acid | 1.0 | | | 1.0 | | |
| | 3-O-dodecyl-L-ascorbic acid | | 1.0 | | | 1.0 | |
| (A') | 3-O-hexadecyl-L-ascorbic acid | | | 1.0 | | | 1.0 |
| (B) | polyoxyethylene(20)sorbitan monooleate | | | | 2.5 | 2.5 | 2.5 |
| other substrate | water | amount making total amount 100.0 | | | | | |
| evaluation items | (1) transparency | x | x | x | ○ | ○ | x |
| | (2) solubilization stability | x | x | x | Δ | Δ | x |
| | (3) preservation stability (coloration) | — | — | — | Δ | Δ | — |
| | (4) sense of use | — | — | — | Δ | Δ | — |
| | (5) odor | — | — | — | Δ | Δ | — |

* In Table, the content of each component is shown in wt %.
** In Table, "—" shows evaluation was not performed.

As shown in Table 1, in samples 1-3 not containing polyoxyethylene sorbitan fatty acid ester as component (B), 3-O-alkyl-L-ascorbic acid was not solubilized well, and a transparent composition was not obtained.

In sample 6 using 3-O-hexadecyl-L-ascorbic acid (A') having an alkyl group having 16 carbon atoms instead of component (A), 3-O-alkyl-L-ascorbic acid was not solubilized well and a transparent composition was not obtained, even though polyoxyethylene sorbitan fatty acid ester as component (B) was contained.

Experimental Example 2

Study of Influence of Nonionic Surfactant

An influence of the kind of the nonionic surfactant on the transparency, solubilization stability, preservation stability and sense of use of a cosmetic composition was studied.

3-O-octyl-L-ascorbic acid or 3-O-dodecyl-L-ascorbic acid as component (A), and nonionic surfactants shown in Table 2 each in the amount shown in Table 2 were added to water to give samples 1-14.

As nonionic surfactants as component (B) and component (B'), the following products (all manufactured by Nikko Chemicals Co., Ltd.) were used.

(i) polyoxyethylene(20)polyoxypropylene(8)cetyl ether; "NIKKOL PBC-44"

(ii) polyoxyethylene(20)sorbitan monostearate; "NIKKOL TS-10V"

(iii) polyoxyethylene(20)sorbitan monooleate; "NIKKOL TO-10V"

(iv) polyoxyethylene(20)polyoxypropylene(4)cetyl ether; "NIKKOL PBC-34"

(v) polyoxyethylene(20)coconut oil fatty acid sorbitan; "NIKKOL TL-10"

(vi) polyoxyethylene(20)oleyl ether; "NIKKOL BO-20V"

(vii) polyoxyethylene(40) hydrogenated castor oil; "NIKKOL HCO-40"

(viii) polyoxyethylene(60) hydrogenated castor oil; "NIKKOL HCO-60"

(ix) polyoxyethylene(100) hydrogenated castor oil; "NIKKOL HCO-10.0"

(x) polyoxyethylene(30)phytosterol; "NIKKOL BPS-30"

Similar to [Experimental Example 1], each sample was evaluated for transparency, solubilization stability, preservation stability, sense of use and odor.

The results are also shown in Table 2.

TABLE 2

| | component | HLB | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|
| (A) | 3-O-octyl-L-ascorbic acid | — | 1.0 | 1.0 | | | | | | | 1.0 | 1.0 | | | | |
| | 3-O-dodecyl-L-ascorbic acid | — | | | 1.0 | 1.0 | 1.0 | 1.0 | 1.0 | 1.0 | | | 1.0 | 1.0 | 1.0 | 1.0 |
| (B) | polyoxyethylene(20)polyoxypropylene(8)cetyl ether | 12.5 | 2.5 | | 2.5 | | | | | | | | | | | |
| | polyoxyethylene(20)sorbitan monostearate | 14.9 | | 2.5 | | | | | | | | | | | | |
| | polyoxyethylene(20)sorbitan monooleate | 15.0 | | | | 2.5 | | | | | | | | | | |
| | polyoxyethylene(20)polyoxypropylene(4)cetyl ether | 16.5 | | | | | 2.5 | | | | | | | | | |
| | polyoxyethylene(20)coconut oil fatty acid sorbitan | 16.9 | | | | | | 2.5 | | | | | | | | |
| | polyoxyethylene(20)oleyl ether | 17.0 | | | | | | | 2.5 | | | | | | | |
| (B') | polyoxyethylene(40) hydrogenated castor oil | 12.5 | | | | | | | | | 2.5 | 2.5 | | | | |
| | polyoxyethylene(60) hydrogenated castor oil | 14.0 | | | | | | | | | | | | 2.5 | | |
| | polyoxyethylene(100) hydrogenated castor oil | 16.5 | | | | | | | | | | | | | 2.5 | |
| | polyoxyethylene(30)phytosterol | 18.0 | | | | | | | | | | | 2.5 | | | 2.5 |
| other substrate | water | — | amount making total amount 100.0 | | | | | | | | | | | | | |
| evaluation items | (1) transparency | | ○ | ○ | ○ | ○ | ○ | ○ | ○ | ○ | Δ | Δ | x | Δ | Δ | x |
| | (2) solubilization stability | | Δ | Δ | Δ | Δ | Δ | Δ | Δ | Δ | x | x | x | x | x | x |
| | (3) preservation stability (coloration) | | Δ | Δ | Δ | Δ | Δ | Δ | Δ | Δ | x | x | x | Δ | Δ | x |
| | (4) sense of use | | Δ | Δ | Δ | Δ | Δ | Δ | Δ | Δ | Δ | Δ | Δ | Δ | Δ | Δ |
| | (5) odor | | Δ | Δ | ○ | ○ | Δ | ○ | ○ | ○ | Δ | Δ | Δ | Δ | Δ | Δ |

In Table, the content of each component is shown in wt %.

As shown in Table 2, in samples 1-8 using, as nonionic surfactant, polyoxyethylene polyoxypropylene alkyl ether (HLB value=12.5 or 16.5), polyoxyethylene sorbitan fatty acid ester (HLB value=14.9, 15.0 or 16.9) and polyoxyethylene alkenyl ether (HLB value=17.0) as component (B), transparent composition was produced.

In contrast, in samples 9 and 11-13 using polyoxyethylene hydrogenated castor oil as component (B') instead of component (B), and in samples 10 and 14 using polyoxyethylene sterol ether as component (B') instead of component (B), a composition having good transparency was not produced, and a composition showing stable solubilization state was not obtained.

Examples 1-5

Cosmetic Composition

According to the formulations shown in Table 3, cosmetic compositions of Examples 1-5 were prepared. In this case, as polyoxyethylene(20)sorbitan monooleate (HLB value=15.0) as component (B), "NIKKOL TO-10V" (manufactured by Nikko Chemicals Co., Ltd.) was used. As an oil agent as component (C), the following product was used.
(i) isopropyl N-lauroyl sarcosinate; "Eldew SL-205" (manufactured by Ajinomoto Co., Inc.)
(ii) N-lauroyl-L-glutamic acid di(phytosteryl/2-octyldodecyl); "Eldew PS-203" (manufactured by Ajinomoto Co., Inc.)
(iii) diisopropyl dilinoleate; "KAK DADIP-R" (manufactured by Kokyu Alcohol Kogyo Co., Ltd.)
(iv) diisostearyl malate; "Haimalate DIS" (manufactured by Kokyu Alcohol Kogyo Co., Ltd.)
(v) monooleyl glyceryl ether; "NIKKOL serachyl alcohol" (manufactured by Nikko Chemicals Co., Ltd.)

Comparative Examples 1-5

Cosmetic Composition

Using the following oil agents (vi)-(x) (component (C')) instead of the oil agents (i)-(v) as component (C) in the above-mentioned Examples 1-5, compositions were similarly prepared and used as Comparative Examples 1-5.
(vi) squalane; "NIKKOL purification olive squalene" (manufactured by Nikko Chemicals Co., Ltd.)
(vii) persic oil; "NIKKOL apricot kernel oil" (manufactured by Nikko Chemicals Co., Ltd.)
(viii) propylene glycol caprylic acid ester; "NIKKOL Sefsol-218" (manufactured by Nikko Chemicals Co., Ltd.)
(ix) cetyl 2-ethylhexanoate; "NIKKOL CIO" (manufactured by Nikko Chemicals Co., Ltd.)
(x) isostearyl alcohol; "Risonol 18SP" (manufactured by Kokyu Alcohol Kogyo Co., Ltd.)

Similar to [Experimental Example 1], the cosmetic compositions of the above-mentioned Examples 1-5 and Comparative Examples 1-5 were evaluated for transparency, solubilization stability, preservation stability, sense of use and odor.

The results are also shown in Table 3.

TABLE 3

| | component | Example | | | | | Comparative Example | | | | |
|---|---|---|---|---|---|---|---|---|---|---|---|
| | | 1 | 2 | 3 | 4 | 5 | 1 | 2 | 3 | 4 | 5 |
| (A) | 3-O-dodecyl-L-ascorbic acid | 1.0 | 1.0 | 1.0 | 1.0 | 1.0 | 1.0 | 1.0 | 1.0 | 1.0 | 1.0 |
| (B) | polyoxyethylene(20)sorbitan monooleate | 2.5 | 2.5 | 2.5 | 2.5 | 2.5 | 2.5 | 2.5 | 2.5 | 2.5 | 2.5 |
| (C) | isopropyl N-lauroyl sarcosinate | 0.25 | | | | | | | | | |
| | N-lauroyl-L-glutamic acid di(phytosteryl/2-octyldodecyl) | | 0.25 | | | | | | | | |
| | diisopropyl dilinoleate | | | 0.25 | | | | | | | |
| | diisostearyl malate | | | | 0.25 | | | | | | |
| | monooleyl glyceryl ether | | | | | 0.25 | | | | | |
| (C') | squalane | | | | | | 0.25 | | | | |
| | persic oil | | | | | | | 0.25 | | | |
| | propylene glycol caprylic acid ester | | | | | | | | 0.25 | | |
| | cetyl 2-ethylhexanoate | | | | | | | | | 0.25 | |
| | isostearyl alcohol | | | | | | | | | | 0.25 |
| other substrate | water | amount making total amount 100.0 | | | | | | | | | |
| evaluation items | (1) transparency | ○ | ○ | ○ | ○ | ○ | Δ | ○ | Δ | ○ | x |
| | (2) solubilization stability | ○ | ○ | ○ | ○ | ○ | Δ | x | Δ | x | x |
| | (3) preservation stability (coloration) | ○ | ○ | ○ | ○ | ○ | x | Δ | x | Δ | Δ |
| | (4) sense of use | ○ | ○ | ○ | ○ | ○ | Δ | Δ | ○ | Δ | Δ |
| | (5) odor | ○ | ○ | ○ | ○ | ○ | ○ | Δ | Δ | Δ | ○ |

In Table, the content of each component is shown in wt %.

As shown in Table 3, the cosmetic compositions of Example 1-5 of the present invention all showed good transparency, were superior in solubilization stability and preservation stability, provided good sense of use free of stickiness, and did not produce a problematic odor.

In contrast, the cosmetic compositions of Comparative Examples 1 and 3 using hydrocarbon oil (squalane) and fatty acid ester of polyvalent alcohol (propylene glycol caprylic m acid ester), respectively, as component (C') instead of the oil agent as component (C) in the present invention were insufficient in the transparency and solubilization stability, poor in preservation stability, and showed remarkable coloration. In addition, the cosmetic compositions of Comparative Examples 2 and 4 using vegetable oil (persic oil) and fatty acid ester (cetyl 2-ethylhexanoate), respectively, as component (C') instead of the oil agent as component (C) showed poor solubilization stability and insufficient preservation stability. The cosmetic composition of Comparative Example 5 using higher aliphatic alcohol (isostearyl alcohol) as component (C') were inferior in the transparency and solubilization stability, and insufficient in the preservation stability. Furthermore, except the cosmetic composition of Comparative Example 3, stickiness was somewhat felt, sufficiently satisfactory sense of use was not afforded, and the cosmetic compositions of Comparative Examples 2-4 had a slight odor.

INDUSTRIAL APPLICABILITY

As described in detail in the above, the present invention can provide a cosmetic composition containing 3-O-alkyl-L-ascorbic acid or a salt thereof, which is superior in transparency, solubilization stability and preservation stability, affords a good sense of use free of stickiness, and poses no odor problem when in use.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A cosmetic composition, comprising:
   (A) at least one 3-O-alkyl-L-ascorbic acid, wherein the alkyl group has 8 to 12 carbon atoms or a salt thereof;
   B) at least one nonionic surfactant selected from the group consisting of a polyoxyethylene polyoxypropylene alkyl ether, a polyoxyethylene sorbitan fatty acid ester, a polyoxyethylene alkyl ether, and a polyoxyethylene alkenyl ether, and having an HLB value of 12.5 to 17; and
   (C) at least one oil agent selected from the group consisting of an amino acid ester, a dimer acid ester, a hydroxy acid ester, an alkyl glyceryl ether, and alkenyl glyceryl ether.

2. The cosmetic composition according to claim 1, wherein said polyoxyethylene polyoxypropylene alkyl ether is an alkylether of polyoxyethylene polyoxypropylene glycol having an average polymerization degree of ethylene oxide of 12 to 30 and an average polymerization degree of propylene oxide of 2 to 8, and the alkyl group is straight chain or branched chain alkyl having about 10 to 16 carbon atoms.

3. The cosmetic composition according to claim 1, wherein said polyoxyethylene sorbitan fatty acid ester is a monoester of sorbitan added with 20 mol to 40 mol of ethylene oxide on average per 1 mol of sorbitan, and a saturated or unsaturated fatty acid having 12 to 18 carbon atoms.

4. The cosmetic composition according to claim 1, wherein said polyoxyethylene alkyl ether is an alkylether of polyethylene glycol having an average polymerization degree of ethylene oxide of 9 to 30, and the alkyl group is a straight chain or branched chain alkyl having 12 to 24 carbon atoms.

5. The cosmetic composition according to claim 1, wherein said polyoxyethylene alkenyl ether is an alkenylether of polyethylene glycol having an average polymerization degree of ethylene oxide of 9 to 30, and the alkenyl group is a straight chain or branched chain alkenyl having 12 to 24 carbon atoms.

6. The cosmetic composition according to claim 1, wherein said amino acid ester is an ester of N-acylamino acid and one or more kinds of alcohol selected from the group consisting of a branched chain saturated lower alcohol having 3 to 5 carbon atoms, a branched chain saturated aliphatic alcohol having 16 to 24 carbon atoms, and a sterol.

7. The cosmetic composition according to claim 1, wherein said dimer acid ester is an ester of dimer dilinoleic acid and one or more kinds of alcohol selected from the group consisting of a branched chain saturated lower alcohol having 3 to 5 carbon atoms, a straight chain or branched chain saturated aliphatic alcohol having 16 to 22 carbon atoms, and sterol.

8. The cosmetic composition according to claim 1, wherein said hydroxy acid ester is an ester of an aliphatic hydroxycarboxylic acid having 2 to 18 carbon atoms and a branched chain saturated aliphatic alcohol having 8 to 18 carbon atoms.

9. The cosmetic composition according to claim 1, wherein said alkyl glyceryl ether is an alkyl glyceryl ether containing an alkyl group having 8 to 22 carbon atoms.

10. The cosmetic composition according to claim 1, wherein said alkenyl glyceryl ether is an alkenyl glyceryl ether containing an alkenyl group having 8 to 22 carbon atoms.

11. The cosmetic composition according to claim 1, which comprises 0.01 wt % to 10 wt % of (A) said at least one 3-O-alkyl-L-ascorbic acid or a salt thereof, relative to the total amount of the cosmetic composition.

12. The cosmetic composition according to claim 1, which comprises 0.01 wt % to 10 wt % of (B) said at least one nonionic surfactant, relative to the total amount of the cosmetic composition.

13. The cosmetic composition according to claim 1, which comprises 0.01 wt % to 5 wt % of (C) said at least one oil agent, relative to the total amount of the cosmetic composition.

14. The cosmetic composition according to claim 1, wherein said amino acid ester is at least one selected from the group consisting of isopropyl N-lauroyl sarcosinate, N-myristoyl-N-methylalaninehexyldecyl, N-myristoyl-N-methyl-β-alanine(phytosterylk/lecyltetradecyl), N-lauroyl-glutamic acid dihexyldecyl, N-lauroylglutamic acid diisostearyl, N-lauroylglutamic acid dioctyldodecyl, N-lauroylglutamic acid bis(hexyldecyl/octyldodecyl), N-stearoyl-glutamic acid dioctyldodecyl, N-lauroylglutamic acid di(cholesteryl/octyldodecyl), N-lauroylglutamic acid di(cholesteryl/behenyl/octyldodecyl), N-lauroylglutamic acid di(phytosteryl/octyldodecyl), and N-lauroylglutamic acid di(octyldodecyl/phytosteryl/behenyl).

15. The cosmetic composition according to claim 1, wherein said dimer acid ester is at least one selected from the group consisting of dimer dilinoleic acid diisopropyl, dimer dilinoleic acid di(isostearyl/phytosteryl), and dimer dilinoleic acid di(phytosteryl/isostearyl/cetyl/stearyl/behenyl).

16. The cosmetic composition according to claim 1, wherein said hydroxy acid ester is a diester of malic acid or tartaric acid and a branched chain saturated aliphatic alcohol having 8 to 18 carbon atoms.

17. The cosmetic composition according to claim 1, wherein said alkyl glyceryl ether is at least one selected from the group consisting of monooctyl glyceryl ether, mono 2-ethylhexyl glyceryl ether, monononyl glyceryl ether, monodecyl glyceryl ether, monoisodecyl glyceryl ether, monoundecyl glyceryl ether, monolauryl glyceryl ether, monomyristyl glyceryl ether, monocetyl glyceryl ether, monostearyl glyceryl ether, monoisostearyl glyceryl ether, monoarachidyl glyceryl ether, and monobehenyl glyceryl ether.

18. The cosmetic composition according to claim 1, wherein said alkenyl glyceryl ether is at least one selected from the group consisting of monooctenyl glyceryl ether, monopalmitoleyl glyceryl ether, monooleyl glyceryl ether, monolinoleyl glyceryl ether, monolinolenyl glyceryl ether, monoricinoleyl glyceryl ether, and monoerucyl glyceryl ether.

* * * * *